United States Patent
Riva et al.

[11] Patent Number: 5,900,928
[45] Date of Patent: May 4, 1999

[54] CONFOCAL BIDIRECTIONAL LASER DOPPLER VELOCIMETRY

[75] Inventors: Charles E. Riva, Les Combes; Benno L. Petrig, Tsanlon; Martial Geiser, Sion, all of Switzerland

[73] Assignee: Institut de Recherche en Ophtalmologie, Sion, Switzerland

[21] Appl. No.: 08/690,477

[22] Filed: Jul. 30, 1996

[51] Int. Cl.⁶ .................................................. G01P 3/36
[52] U.S. Cl. .......................................... 356/28.5; 600/479
[58] Field of Search ......................... 356/28.5; 128/866, 128/691, 745

[56] References Cited

U.S. PATENT DOCUMENTS

| | | |
|---|---|---|
| 3,915,572 | 10/1975 | Orloff . |
| 4,026,655 | 5/1977 | Gunter, Jr. . |
| 4,109,647 | 8/1978 | Stern et al. . |
| 4,142,796 | 3/1979 | Riva . |
| 4,166,695 | 9/1979 | Hill et al. . |
| 4,346,991 | 8/1982 | Gardner et al. . |
| 4,387,993 | 6/1983 | Adrian . |
| 4,402,601 | 9/1983 | Riva . |
| 4,470,696 | 9/1984 | Ballard . |
| 4,596,254 | 6/1986 | Adrian et al. . |
| 4,780,605 | 10/1988 | Tiemann . |
| 4,854,705 | 8/1989 | Bachalo . |
| 4,907,887 | 3/1990 | Leonard et al. . |
| 5,074,307 | 12/1991 | Aizu et al. . |
| 5,129,400 | 7/1992 | Makino et al. . |
| 5,308,919 | 5/1994 | Minnich . |
| 5,436,130 | 7/1995 | Mathies et al. . |
| 5,549,114 | 8/1996 | Peterson et al. ...................... 128/691 |
| 5,620,000 | 4/1997 | Zinser et al. ........................ 128/666 |

OTHER PUBLICATIONS

Wang et al., "Characterization of fluid flow velocity by optical Doppler tomography," Optics Letters vol. 20, No. 11 Jun. 1, 1995, pp. 1337–1339.

Erskine et al., "White–light velocimetry," Nature vol. 377, 28 Sep. 1995, pp. 317–320.

Primary Examiner—Mark Hellner
Attorney, Agent, or Firm—Dan M. de la Rosa

[57] ABSTRACT

An apparatus is provided for the measurement of the velocity of blood flowing within a blood vessel of an eye wherein the apparatus includes a light source for producing a source beam of light and an optical element for applying the source beam of light to the blood vessel to permit the blood flowing within the blood vessel to scatter a portion of the source beam of light and produce bidirectional scattered beams. A detector system for detecting the bidirectional scattered beams provides signals representative of the scattered beams. The light source and the detector system are disposed in a confocal relationship. An output representative of the velocity of the blood flow velocity is produced in accordance with the signals. The light source and the detector system include respective pinholes wherein the respective pinholes are disposed in the confocal relationship. The blood vessel is conjugate with the respective pinholes of the light source and the detector system. The angle between the bidirectional scattered beams is determined and a measurement of blood flow velocity is determined according to the angle.

20 Claims, 6 Drawing Sheets

CONFOCAL BIDIRECTIONAL LASER DOPPLER VELOCIMETRY

BACKGROUND OF THE INVENTION

1) Field of the Invention

This invention relates to a method and an apparatus for determining the velocity of particles moving through a tube and, in particular, to a method and an apparatus for determining the velocity of blood flowing in a vessel of the eye.

2) Prior Art

As was pointed out in U.S. Pat. No. 4,142,796, issued Mar. 6, 1979, to Charles E. Riva, and elsewhere, the ability to measure the velocity of blood flowing in a single blood vessel or in a capillary bed is very useful for medical purposes. Impairment of the blood flow in the tissues of the ocular fundus, or the retina of the eye, is associated with a large number of diseases that can lead to grave visual disorders.

The feasibility of using laser Doppler velocimetry to measure blood flow in individual retinal vessels was demonstrated in 1972 by Riva et al. (C. E. Riva, B. Ross and G. B. Benedek, Investigative Ophthalmology, Vol. 11, pps. 936 et seq., November 1972). Riva et al. measured the Doppler-shift frequency spectrum of laser light scattered from red blood cells flowing in a retinal artery of an anesthetized rabbit. The maximum Doppler frequency shift $f_{max}$ arising from the light scattered by the red blood cells flowing at the maximum velocity $V_{max}$ was estimated from the spectrum of the scattered light. $V_{max}$ was calculated from $f_{max}$ and from estimates of the intraocular scattering geometry using the general relation:

$$V_{max} = \frac{\lambda f_{max}}{n(\cos\theta_s - \cos\theta_i)}$$

where $\lambda$ is the wavelength in vacuo of the incident laser light, n is the refractive index of the flowing medium, $\theta_i$ is the intraocular angle between the incident beam and the blood flow direction, and $\theta_s$ is the intraocular angle between the collected scattered light beams and the blood flow direction. It was assumed that the incident laser beam was perpendicular to the blood flow direction.

It has also been shown (G. T. Feke and C. E. Riva, J. Opt. Soc. Am. Vol. 68, pps. 526 et seq., 1978) that $f_{max}$ can be determined from Doppler-shift frequency spectra obtained from human retinal vessels using short measurement times. Furthermore, it has been shown that $V_{max}$ can be determined by a procedure involving the collecting of light scattered by red blood cells in two distinct directions, separated by a known angle (C. E. Riva, G. T. Feke, B. Eberli and V. Bernary, Applied Optics, Volume 18, pps. 2301 et seq., Jul. 1, 1979). It has been determined that analysis of the collected light yields an absolute measurement of $V_{max}$ that is independent of the exact orientation of the incident and scattered light beams with respect to the blood flow direction.

In U.S. Pat. No. 4,402,601, issued on Sep. 6, 1983, to Charles E. Riva, bidirectional LDV was performed using an apparatus, the basic component of which was a standard retinal camera. The need for a contact lens was eliminated, and the laser beam was delivered to the eye through the fundus illumination optical system of the camera. The device taught by Riva in U.S. Pat. No. 4,402,601 greatly simplified the technique of retinal blood flow measurement.

In the device taught by Riva, bidirectional laser Doppler velocimetry was used to permit absolute measurements of the velocity of red blood cells flowing through retinal vessels. In this technique the Doppler-shift frequency spectra of laser light scattered from the red blood cells were recorded for two directions of the scattered light, while the direction of the incident beam remained constant. The Doppler-shift frequency spectra, when obtained in short measurement times, exhibited large fluctuations in spectral power up to a cutoff at a frequency $f_{max}$ that arose from light scattered by red blood cells flowing at the maximum velocity $V_{max}$ at the center of the blood vessel. $V_{max}$ was obtained from the Doppler-shift frequency spectra using the relation:

$$V_{max} = \frac{\lambda \alpha f}{n \Delta \alpha \cos\beta}$$

wherein $\lambda$ was the wavelength of the incident laser beam used to perform the measurement, $\Delta f = f_{2\ max} - f_{1\ max}$ was the difference between the cutoff frequencies obtained from Doppler-shift frequency spectra recorded in two directions, $\overline{K}_1$ and $\overline{K}_2$, n was the index of refraction of the flowing medium, a was the angle between vectors $\overline{K}_1$ and $\overline{K}_2$ and $\beta$ was the angle between the vector $V_{max}$ and its projection on the plane defined by the vectors $\overline{K}_1$ and $\overline{K}_2$.

The first absolute measurements of $V_{max}$ were obtained by Riva using a standard slitlamp microscope in conjunction with a low-vacuum corneal contact lens. The use of a contact lens considerably simplified the determination of the scattering geometry because the lens eliminated the corneal refraction of the Doppler shifted light. Several problems arose, however, when the technique was applied to human subjects: (a) there was a risk of corneal abrasion and infect (b) there was poor motion stabilization of the target retina because the fellow (non-target) eye was used for target fixation; (c) changes in intraocular pressure caused by application of the contact lens could affect retinal blood flow; and (d) the slitlamp instrument did not allow Doppler-shift frequency spectra to be simultaneously recorded for two directions of the scattered light or the determination of $V_{max}$ in vertical vessels.

While the method taught by Riva provided reliable velocity measurements, it suffered from inherent drawbacks with regard to alignment and depth resolution. Regarding alignment in the Riva method, the procedure for measuring blood velocity in a vessel consisted of focusing a laser beam on the vessel. Two beams of the light scattered by the moving particles were optically selected and focused in a plane by a lens. The two scattered light beams were collected by two optical fibers which transferred them to two photodetectors. The input apertures of the optical fibers transmitting the scattered light to the photo-detectors were moved to the two focused beams using x-y microdrives. This procedure was time consuming, particularly when the incident beam was moved to a number of different vessels, as was the case when several retinal or conjunctival vessels were measured.

The depth resolution of these measurements was determined by the optics of the eye and the optical systems used to illuminate the vessel and to detect the scattered light. In a fundus camera arrangement, for example, the resolution was insufficient to separate light scattered by the different layers of the fundus so that measurements from retinal vessels could be affected by light scattered from red blood cells moving in the choriocapillaries. This was the case, in particular, when the velocity of the moving red blood cells was measured in small retinal blood vessels.

Therefore, an object of the optical system of the present invention is to overcome the inherent drawbacks with regard to alignment and depth resolution, as well as other drawbacks in the prior art, by providing a method and apparatus for self-alignment when measuring the velocity of moving particles such as red blood cells in individual blood vessels combining the principles of confocal imaging and bidirectional laser velocimetry and incorporating the apparatus into a device that allows viewing of the blood vessel and the surrounding media.

More particularly, it is an object of the optical system of the present invention to measure the velocity of moving particles such as red blood cells in individual blood vessels of a vascular bed such as the conjunctiva and the iris in the anterior part of the eye or in the retina in the fundus of the eye.

Another object of the optical system of the present invention is to provide an instrument that is more compact and easier to use than prior art velocimetry instruments.

Another object of the optical system of the present invention is to provide better spatial definition than the spatial definition available in prior art velocimetry instruments.

Another object of the optical system of the present invention is to provide an instrument having substantially common path propagation of the illumination beam and the scattered detector beams.

Another object of the optical system of the present invention is to provide adaptability to existing ophthalmic instruments such as fundus cameras, slitlamps and laser scanning ophthalmoscopes with minimal modification of the existing instruments.

Briefly the present invention is a method and apparatus for measuring the speed of particles moving in the same direction, such as red blood cells moving in individual blood vessels, combining the principles of confocal imaging and bidirectional laser Doppler velocimetry. In the method of the invention the moving particles are illuminated by a laser beam and the light scattered by the moving particles is detected along two directions by two photodetectors. The optical systems for illuminating the moving particles and for detecting the scattered light are arranged in a confocal mode. The scattered light contains components corresponding to Doppler-shifted light from the moving particles and components corresponding to the unshifted light corresponding to the light scattered by nonmoving structures (reference beam). The shifted and unshifted components are caused to interfere at the surface of each photodetector. Electric signals from the photodetectors thus contain a spectrum corresponding to the optical spectrum of the scattered light shifted down to lower frequencies by an amount equal to the frequency of the incident laser light. The electrical signals are filtered, amplified and digitized. A computer algorithm removes the noise component from the digitized signals to determine the noise free spectrum. The maximum frequency shift, corresponding to the maximum velocity of the particles (centerline velocity), is then determined from the noise free spectrum. In the bidirectional mode, the signals from the two detectors are analyzed to obtain two maximum frequency shifts. From the two maximum frequency shifts, the frequency of the incident laser beam, the angle between both scattered beams, and the maximum velocity of the moving particles are obtained.

SUMMARY OF THE INVENTION

An apparatus is provided for the measurement of the velocity of blood flowing within a blood vessel of an eye wherein the apparatus includes a light source for producing a source beam of light and an optical element for applying the source beam of light to the blood vessel to permit the blood flowing within the blood vessel to scatter a portion of the source beam of light and produce bidirectional scattered beams. A detector system for detecting the bidirectional scattered beams provides signals representative of the scattered beams. The light source and the detector system are disposed in a confocal relationship. An output representative of the velocity of the blood flow velocity is produced in accordance with the signals.

DETAILED DESCRIPTION OF THE INVENTION

Figure 1:
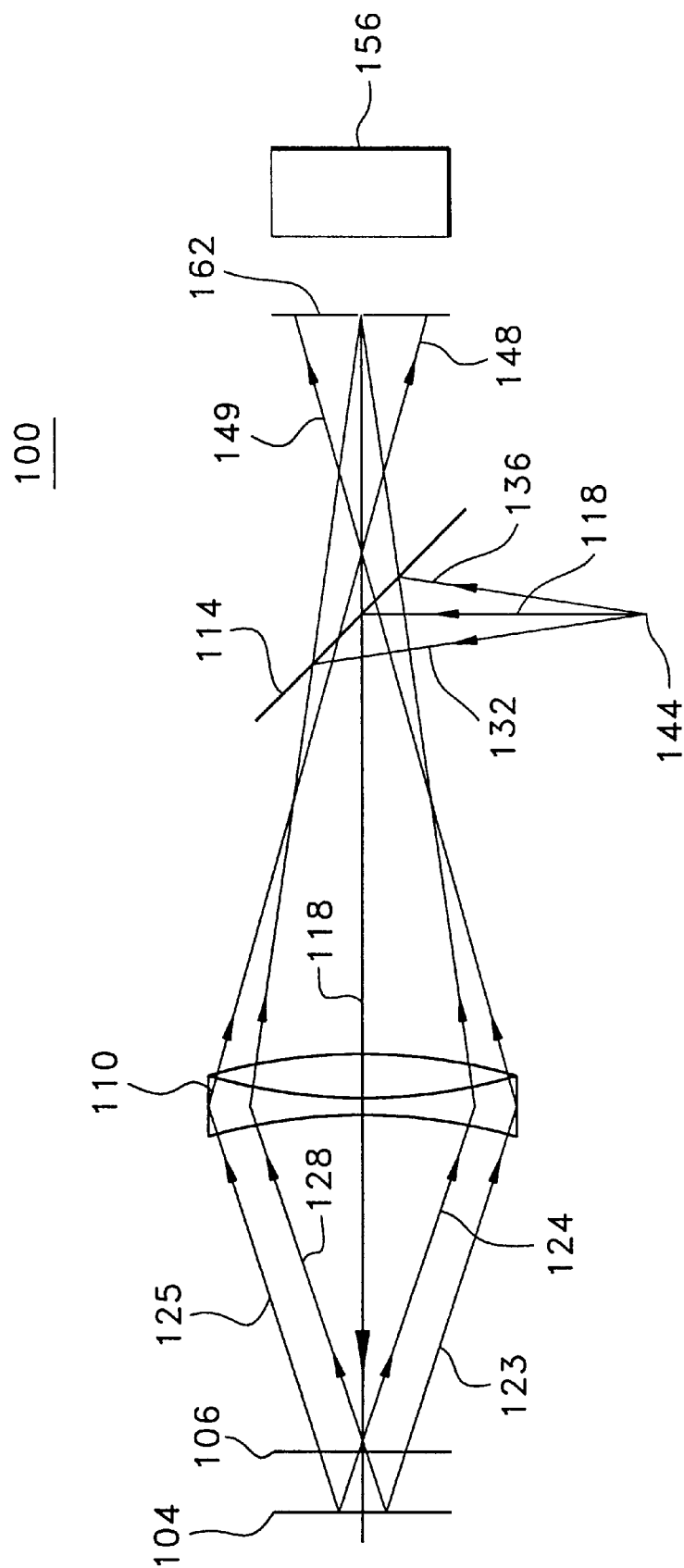
FIG. 1 is a schematic representation of a confocal bidirectional optical system in accordance with present invention.

Referring now to FIG. 1, there is shown confocal bidirectional optical system 100. Within confocal bidirectional optical system 100, source light beam 118 from light source 144 is applied to beam splitter 114. It will be understood that light source 144 is a point source of coherent light. Light applied to beam splitter 114 is received by dual optical system 110 and transmitted by way of dual optical system 110. Light transmitted in this manner by dual optical system 110 is applied to a partially transparent object 106 such as a blood vessel 106.

Part of the incident light from point light source 144 applied to object 106 is back scattered by object 106 as scattered beams 124, 128. Scattered beams 124, 128 are collected by dual optical system 110 and transmitted by dual optical system 110. Light transmitted in this manner by dual optical system 110 is applied by dual optical system 110 to beam splitter 114. Thus dual optical system 110 and beam splitter 114 perform the dual operations of transmitting the light incident upon object 106 and transmitting the light scattered by object 106.

A portion of the light applied to beam splitter 114 by dual optical system 110 passes through beam splitter 114 and is imaged upon detector pinhole 162. Within confocal bidirectional optical system 100 detector pinhole 162 is confocal with point light source 144. Additionally, object 106, detector pinhole 162 and light source 144 are conjugate. It will be understood by those skilled in the art that by conjugate it is meant that detector pinhole 162, light source 144 and object 106 are images of each other.

Light emerging from detector pinhole 162 falls upon photodetector system 156 and is detected by photodetector system 156. A major advantage of confocal bidirectional optical system 100 is that light scattered by objects other than object 106, such as object 104, are not in focus and are not imaged upon pinhole 162. For example, light back scattered by object 104 as scattered beams 123, 125 is also collected by dual optical system 110 and transmitted toward detector pinhole 162. However, light from scattered beams 123, 125 is transmitted toward detector pinhole 162 as beams 148, 149, which are out of focus and are not imaged on detector pinhole 162. Because objects such as object 104 are not imaged upon detector pinhole 162, they are not detected by photodetector system 156.

When adapting confocal bidirectional optical system 100 for use when object 106 is a blood vessel 106, the velocity of the blood flowing within blood vessel 106 can be measured using the Doppler-shifted back-scattered light of source light beam 118 focused upon blood vessel 106. The principal requirements of this measurement method are (1) the light focused upon blood vessel 106 must be coherent light, (2) the back-scattered light must be detected in two different directions, (3) the angle between the two directions of back-scattered light must be known, and (4) there must be a spatial extension of source light beam 118 on blood vessel 106.

More specifically, when the method of the present invention is performed upon an eye means for observing where source light beam 118 is focused and means for aiming source light beam 118 at different locations on the retina, the iris or the conjunctiva are required. Also required to adapt confocal bidirectional optical system 100 to measurements within an eye are means for avoiding glare reflection in the detection and the ability to enter source light beam 118 at different locations in the pupil. Furthermore, means to align scattered beams 124, 128 and the direction of the blood velocity vector in the same plane are also required.

Figure 2:
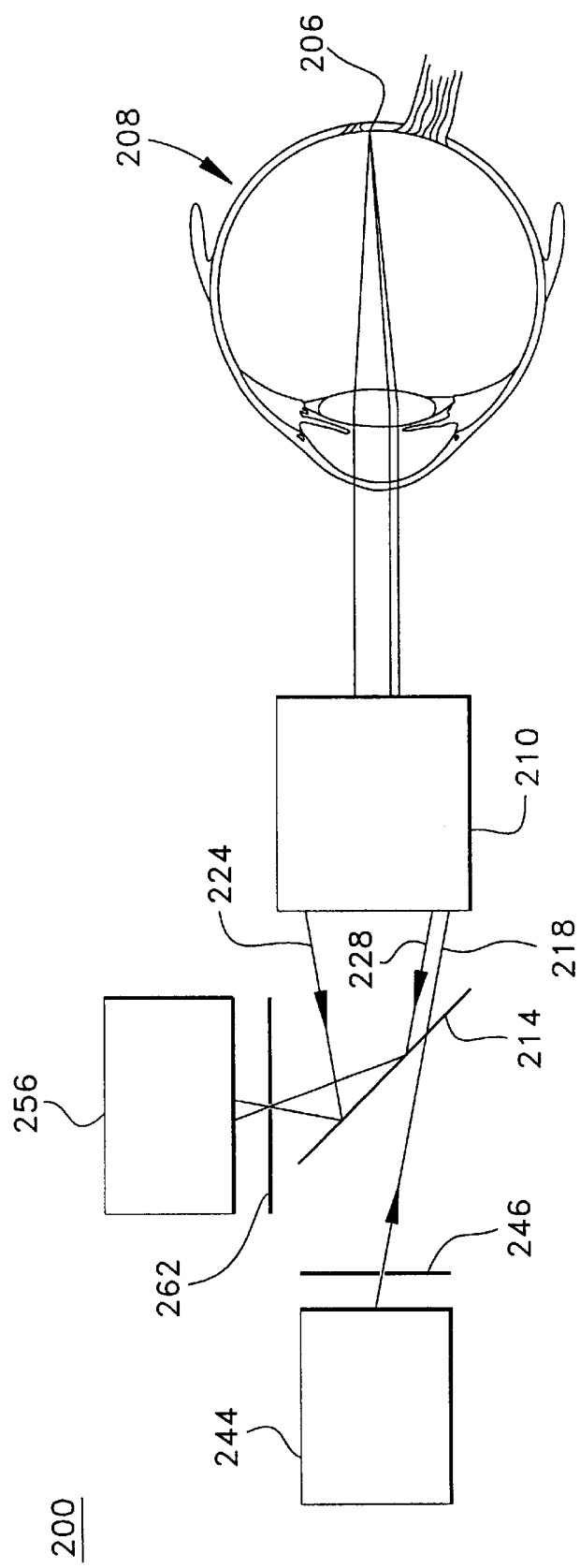
FIG. 2 is a block diagram representation of a confocal bidirectional optical system in accordance with the present invention applied to performing a blood velocity measurement within an eye.

Referring now to FIG. 2, there is shown confocal bidirectional optical system 200 of the present invention. Confocal bidirectional optical system 200 is adapted to apply the principles of confocal bidirectional laser Doppler velocimetry to the measurement of the velocity of blood flow within blood vessel 206 of eye 208.

Confocal bidirectional optical system 200 includes point light source 244 for providing source light beam 218. In the preferred embodiment of confocal bidirectional optical system 200 point light source 244 includes two lasers for providing two source light beams. One source light beam, operating at a frequency not visible to the human eye, is used for probing and measuring eye 208 and measuring blood flow velocity within eye 208 in accordance with the method of the invention. The other source light beam, operating at a visible frequency, is provided for aiming the probing and measuring beam. The probing and measuring beam and the aiming beam are combined to form source light beam 218.

Source light beam 218 from point light source 244 passes through source pinhole 246. A portion of source light beam 218 passing through source pinhole 246 passes through beam splitter 214. The portion of source light beam 218 passing through beam splitter 214 is imaged by dual optical system 210 and applied to blood vessel 206 within eye 208. In the preferred embodiment of confocal bidirectional optical system 200 dual optical system 210 is adapted to aim source light beam 218 at different locations within eye 208.

A portion of the focused light applied to eye 208 by dual optical system 210 is back scattered by blood vessel 206, within eye 208. The back-scattered light is collected by dual optical system 210 and applied to beam splitter 214 as scattered beams 224, 228. A portion of scattered beams 224, 228 applied to beam splitter 214 by dual optical system 210 is reflected by beam splitter 214 and focused on detector pinhole 262. Photodetector system 256, located behind detector pinhole 262, collects scattered beams 224, 228, wherein the angle between beams 224, 228 is known. The source pinhole 246 and the detector pinhole 262 are images of blood vessel 206. Both the incident beam and the selected back scattered beams follow the same path. Because pinholes 246, 262 are confocal in this manner, they are self-aligned and there is no need for the alignment microdrives of the prior art.

Figure 3:
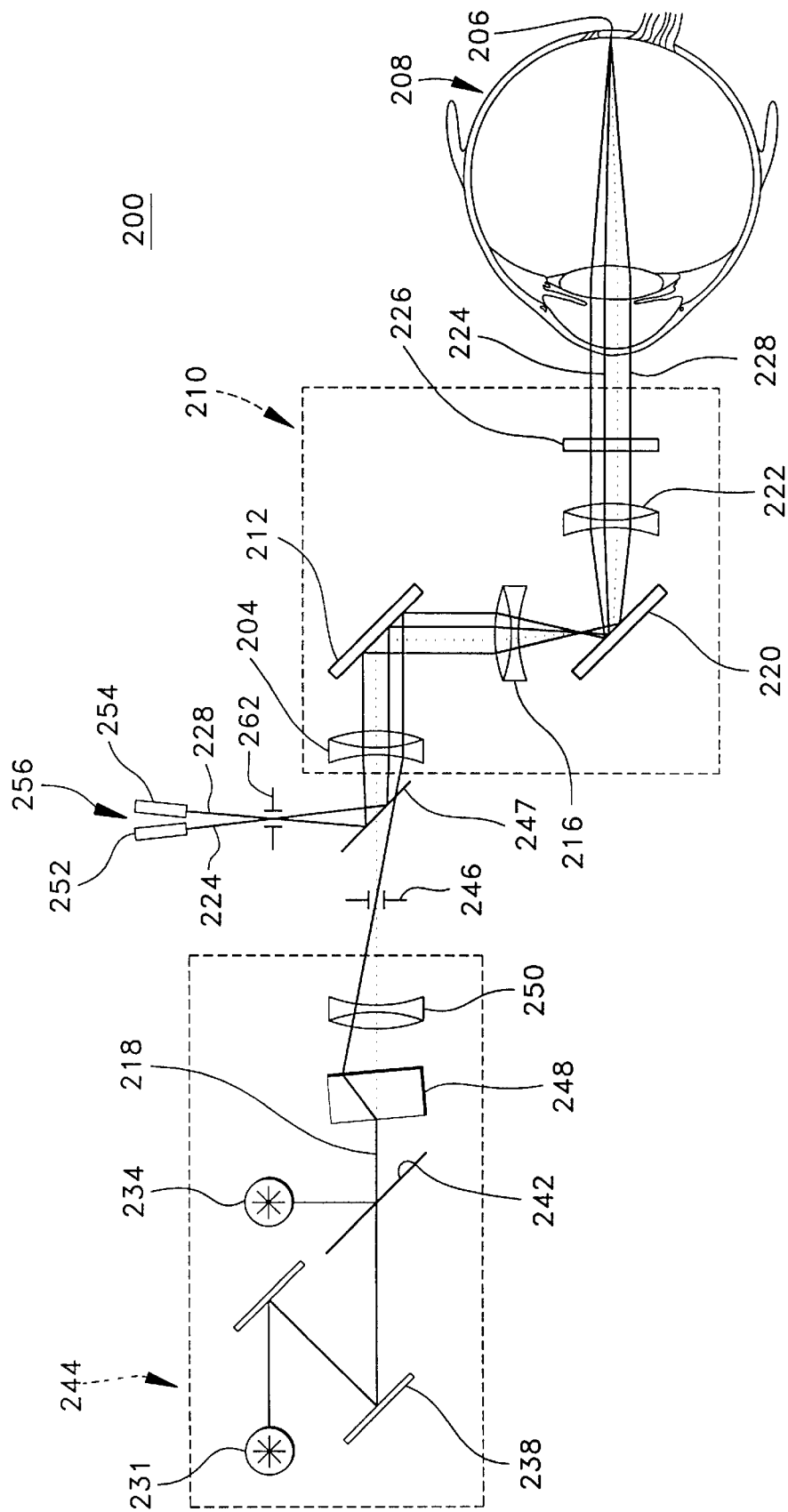
FIG. 3 is a more detailed schematic representation of the confocal bidirectional optical system of FIG. 2.

Referring now to FIG. 3, there is shown a more detailed representation of confocal bidirectional optical system 200. Within confocal bidirectional optical system 200, point light source 244 contains lasers 231, 234. Laser 234 emits light energy in the near infrared range which is not visible and is used for the Doppler velocity measurements of the invention. Laser 231 produces light at a visible frequency and is used to locate the light from laser 234. The laser beams from lasers 231, 234 are brought onto the same path, for example with an adjustable system of mirrors 238 and a beam splitter 242. The light beams combined in this way form source light beam 218 which is focused by objective 250 onto source pinhole 246. Point light source 244 can be polarized so that the polarization state can be used to discriminate reflected light.

Both laser beams forming source light beam 218 are focused on infinity and pass through plane parallel plate 248 which can be made of glass. Parallel plate 248 does not alter the focalization of the beams forming source light beam 218. However, parallel plate 248 does alter the radial distances of the beams relative to the optical axis. Thus, rotation of parallel plate 248 allows source light beam 218 to enter at different locations of the pupil of eye 208 without changing the focalization on the retina.

Source pinhole 246 can be imaged upon vessels in a variety of locations within eye 208 by means of dual optical system 210. When measurements are obtained from a retinal blood vessel 206 at the back of eye 208, the dioptric system of eye 208 formed by the cornea and the crystalline lens is placed after the $\lambda/4$ plate 226 of dual optical system 210 to cause source light beam 218 to focus on vessel 206. When measurements are obtained from blood vessel 206 in the conjunctiva or the iris within eye 208, objective lens 222 is used to focus source light beam 218 on vessel 206.

Dual optical system 210 of confocal bidirectional optical system 200 includes collecting lens 204. Collecting lens 204 is adapted to compensate refractive errors of eye 208. Dual optical system 210 also includes lenses 216, 222. Lenses 216, 222 are adapted to image the entrance to the pupil of eye 208 on movable mirror 212 of dual optical system 210. Thus movable mirror 212 is a pupil image. Rotation of movable mirror 212 causes displacement of the focus point within the retina of eye 208 and a change of direction of source light beam 218 at the entrance of eye 208.

In various embodiments of the present invention lens 222 of dual optical system 210 can be the objective lens of a standard fundus camera, a conventional laser scanning ophthalmoscope or a conventional slitlamp. Thus in the preferred embodiment of dual optical system 210 mirror 220 is semitransparent in order to permit observation of the fundus of eye 208, the injection of probing beam 118 and the collection of scattered light beams 224, 228.

Light that is back scattered by moving red blood cells within blood vessel 206 is received by dual optical system 210 and focused upon detector pinhole 262 by collecting lens 204 of dual optical system 210. Detector pinhole 262 is conjugate to source pinhole 246. Photodetectors 252, 254 behind detector pinhole 262 are adapted to rotate around the optical axis and thus collect different beams of light around the optical axis. The selected beams of scattered light correspond to scattered beams 224, 228, which are received by photodetectors 252, 254 respectively.

Scattered light beams 224, 228 received by photodetectors 252, 254 of photodetector system 256 are converted into electrical signals in a conventional manner by photodetectors 252, 254. The electrical signals provided by photodetectors 252, 254 represent Doppler-shifted frequency components of scattered light beams 224, 228 and components of scattered light beams 224, 228 that are not Doppler shifted. The electrical signals are filtered, amplified, digitized and processed by a computer (not shown) in order to determine the velocity of the moving particles in blood vessel 206 within eye 208 being measured by confocal bidirectional optical system 200 of the present invention. The computer is programmed to provide an output representative of the velocity of the moving particles within blood vessel 206.

Confocal bidirectional optical system 200 can be used in combination with a standard fundus camera system, a laser scanning ophthalmoscope or a slitlamp, with or without a contact lens placed on the cornea. The combination of the subject invention and these devices allows observation of incident source light beam 218 together with blood vessel 206 as well as the areas surrounding blood vessel 206. For example, combining the subject invention with a fundus camera permits an observer to view the retina at the back of eye 208 and view blood vessel 206 containing the moving red blood cells for which velocity is measured.

Figure 4:
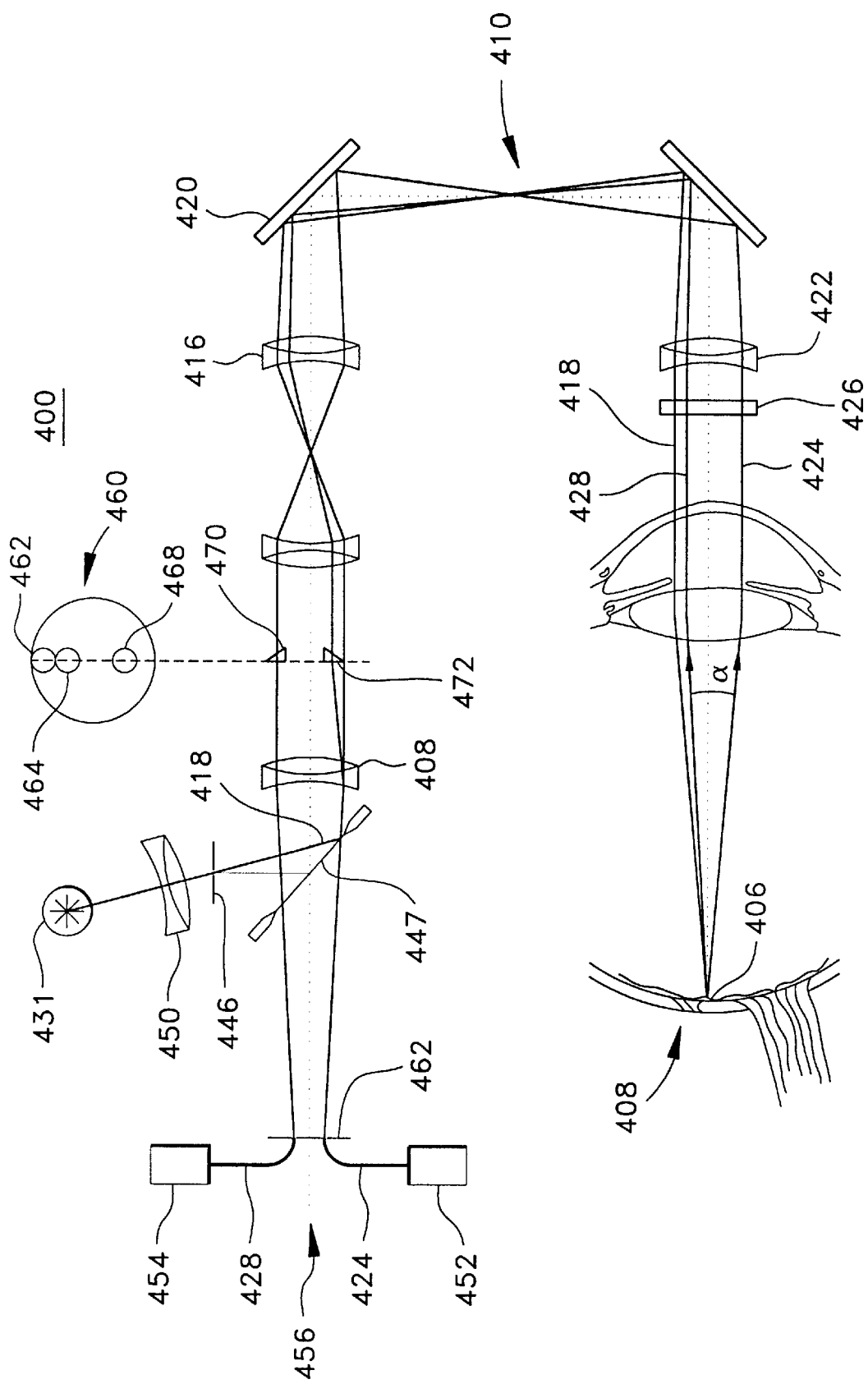
FIG. 4 is a schematic representation of an alternate embodiment of the confocal bidirectional optical system of FIG. 3.

Referring now to FIG. 4, there is shown confocal bidirectional optical system 400 Confocal bidirectional optical system 400 is an alternate embodiment of confocal bidirectional optical system 200. Within dual optical system 410 of confocal bidirectional optical system 400 aperture disk 460 having three disk openings 462, 464, 468 is provided. The distance between disk openings 462, 464 of aperture disk 460, along with the refractive index of eye 208 and the axial length of eye 208, define the interocular angle a between scattered light beams 424, 428 focused by dual optical system 410. Aperture disk 460 within confocal bidirectional optical system 400 is a pupil image. Movable mirror 420 is also a pupil image within optical system 400.

Optical component 472 is placed in the optical path between disk opening 464 of aperture disk 460 and blood vessel 406. Additionally, optical component 470 is placed in the optical path between disk opening 468 of aperture disk 460 and blood vessel 406. Optical components 470, 472 refract light beams 424, 428 in directions different from each other and different from the rest of the scattered light so that only scattered beams 424, 428 are detected by photodetectors 452, 454. Optical components 470, 472 can be prisms, holograms including computer generated holograms, binary optics or lenses.

Aperture disk 460 is adapted to be rotatable around the optical axis. Thus, the segment of aperture disk 460 containing disk aperture 464 and disk aperture 468 can be aligned with the direction of motion of the moving particles within blood vessel 406 being measured within eye 408 by confocal bidirectional optical system 400.

Photodetectors 452, 454 of photodetector system 456 can be rotated in the plane of the image of blood vessel 406 so that they can be located to receive scattered light beams 424, 428 that are focused in this plane. Alternately, photodetectors 452, 454 can be replaced by a circular array of fixed photodetectors from which two photodetectors are electrically selected to receive scattered light beams 424, 428.

Source light beam 418 is aimed at the desired location of the blood vessel in eye 406 by means of scanning mirrors 420. In the preferred embodiment of the invention scanning mirrors 420 can be placed in the plane of the pupil of eye 408.

Figure 5:
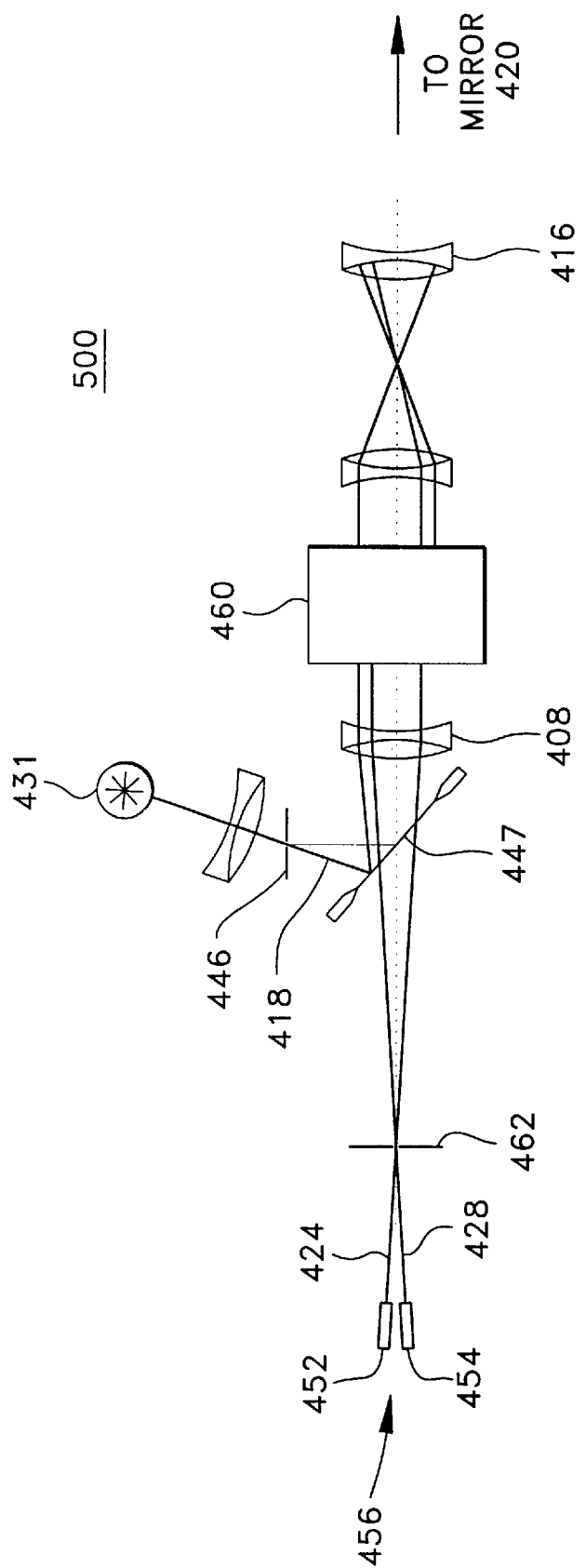
FIG. 5 is a schematic representation of an alternate embodiment of a portion of the confocal bidirectional optical system of FIG. 4.

Referring now to FIG. 5, there is shown confocal bidirectional optical system 500. Confocal bidirectional optical system 500 is an alternate embodiment of a portion of confocal bidirectional optical system 400. An alternate arrangement for the alignment of scattered light beams 424, 428 with photodetectors 452, 454 is provided within confocal bidirectional optical system 500.

Within confocal bidirectional optical system 500 the separation and rotation of source light beam 418 from laser 431 and scattered light beams 424, 428 are performed at aperture disk 460. Aperture disk 460 of optical system 500 is a pupil image as previously described with respect to aperture disk 460 of optical system 400.

The detection of scattered light beams 424, 428 within confocal bidirectional optical system 500 is performed using photodetectors 452, 454 as previously described with respect to confocal bidirectional optical system 400. However, rotation and selection of scattered beams 424, 428 is performed with an image reversing prism such as a Dove prism. When rotation and selection are performed in this manner photodetectors 452, 454 of photodetector system 456 can be fixed.

Figure 6:
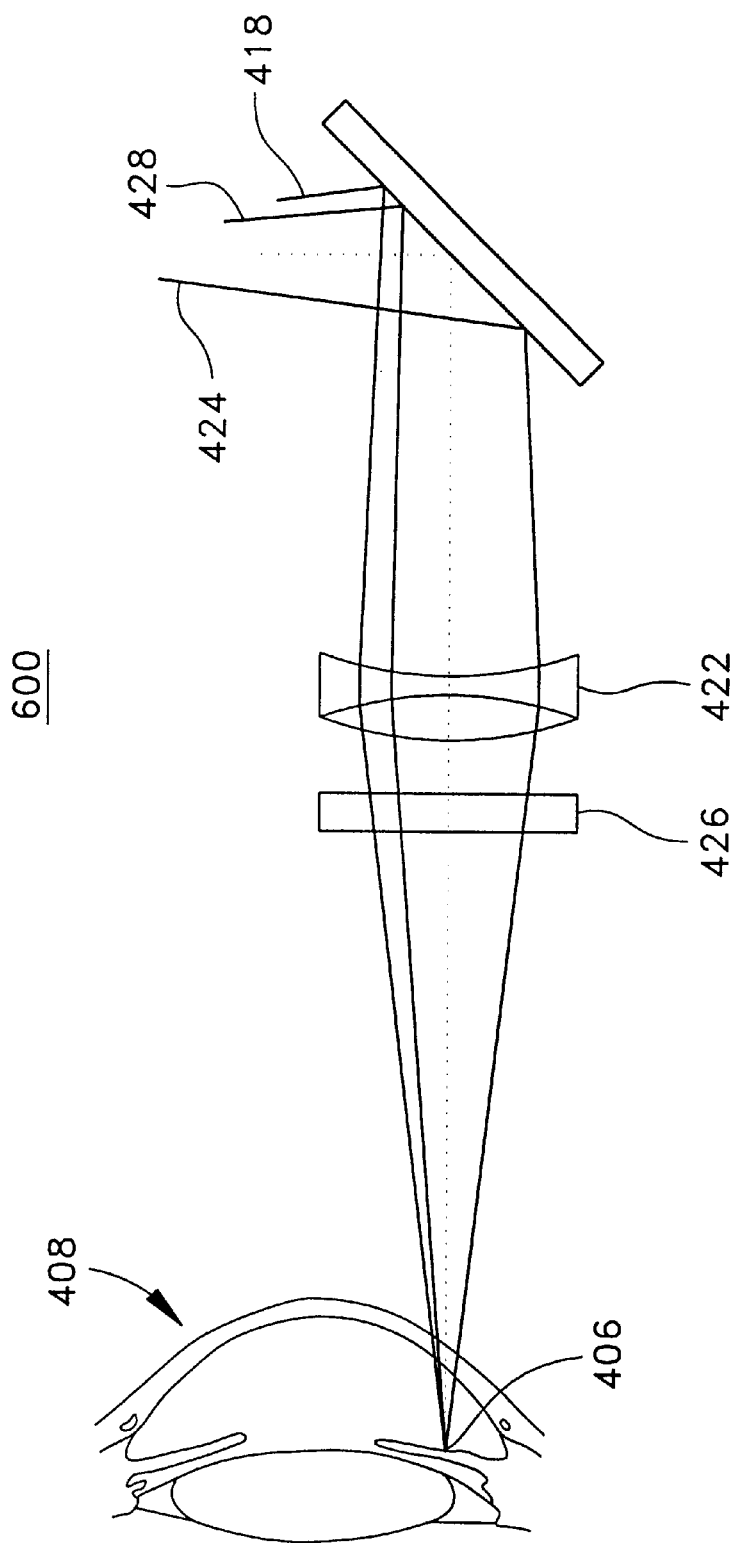
FIG. 6 is an alternate embodiment of a portion of the confocal bidirectional optical system of FIG. 4.

Referring now to FIG. 6, there is shown confocal bidirectional optical system 600. Confocal bidirectional optical system 600 is an alternate embodiment of a portion of confocal bidirectional optical system 400. Optical system 600 is adapted to advantageously measure blood flow velocity in blood vessel 406 located in the conjunctiva or in the iris of eye 408. Using confocal bidirectional optical system 600 source light beam 418 can be focused on blood vessel 406 of the conjunctiva or the iris of eye 406 using lens 422.

The present invention may be embodied in other specific forms without departing from its spirit or essential attributes, and, accordingly, reference should be made to the appended claims and the accompanying drawings as indicating the scope of the invention.

We claim:

1. An apparatus for measuring the velocity of blood flowing within a blood vessel of an eye, comprising;
    a light source for producing a source beam of light;
    an optical element for applying said source beam of light to said blood vessel to permit said blood flowing within said blood vessel to scatter a portion of said source beam of light and produce bidirectional scattered beams;
    a detector system for detecting said bidirectional scattered beams to provide signals representative of said bidirectional scattered beams;
    said light source and said detector system being disposed in a confocal relationship; and
    a signal processor for producing an output representative of said velocity of said blood flowing within said blood vessel in accordance with said signals.

2. The measurement apparatus in accordance with claim 1, wherein said light source and detector system comprise respective pinholes.

3. The measurement apparatus in accordance with claim 2, wherein said respective pinholes are disposed in said confocal relationship.

4. The measurement apparatus in accordance with claim 1, wherein said blood vessel is conjugate with said light source and said detector system.

5. The measurement apparatus in accordance with claim 1, wherein the angle between said bidirectional scattered beams is known.

6. The measurement apparatus in accordance with claim 5, wherein a measurement of said velocity of said blood flowing through said blood vessel is determined in accordance with said angle.

7. The measurement apparatus in accordance with claim 1, wherein said optical element comprises a dual optical system for simultaneously transmitting said source beam of light and said bidirectional scattered beams.

8. The measurement apparatus in accordance with claim 7, wherein said dual optical system focuses selected bidirectional scattered beams upon said detector system and applies unselected scattered beams to said detector system unfocused.

9. The measurement apparatus in accordance with claim 1, wherein said source beam of light comprises coherent light.

10. The measurement apparatus in accordance with claim 1, wherein said bidirectional scattered beams comprise Doppler shifted light.

11. The measurement apparatus in accordance with claim 10, wherein a measurement of said velocity of said blood flowing in said blood vessel is determined in accordance with the Doppler shift of said Doppler shifted light.

12. The measurement apparatus in accordance with claim 1, further comprising means for aligning said bidirectional scattered beams and the direction of a speed vector of said velocity of said blood flowing within said blood vessel upon the same plane.

13. The measurement apparatus in accordance with claim 1, wherein said detector system comprises two photodetectors, each photodetection being positioned to receive one of said bidirectional scattered beams.

14. The measurement apparatus in accordance with claim 1, wherein said light source comprises a plane parallel plate for transmitting said source beam of light through said plane parallel plate and changing focalization of said source beam of light by rotating said plane parallel plate.

15. The measurement apparatus in accordance with claim 1, further comprising a fundus camera.

16. The measurement apparatus in accordance with claim 1, further comprising a laser scanning ophthalmoscope.

17. The measurement apparatus in accordance with claim 1, further comprising a slitlamp.

18. The measurement apparatus in accordance with claim 1, further comprising an aperture disk.

19. The measurement apparatus in accordance with claim 18, wherein said aperture disk is adapted to be a pupil image.

20. The measuring apparatus in accordance with claim 1, wherein said source beam of light comprises two beams of light having differing wavelengths.

\* \* \* \* \*